United States Patent
Miyake

(10) Patent No.: US 9,594,068 B2
(45) Date of Patent: Mar. 14, 2017

(54) ABNORMALITY DETECTION SYSTEM OF ENGINE EXHAUST SYSTEM

(71) Applicant: Teruhiko Miyake, Shizuoka (JP)

(72) Inventor: Teruhiko Miyake, Shizuoka (JP)

(73) Assignee: Toyota Jidosha Kabushiki Kaisha, Toyota-shi, Aichi (JP)

( * ) Notice: Subject to any disclaimer, the term of this patent is extended or adjusted under 35 U.S.C. 154(b) by 0 days.

(21) Appl. No.: 14/423,289

(22) PCT Filed: Nov. 16, 2012

(86) PCT No.: PCT/JP2012/079814
§ 371 (c)(1),
(2) Date: Feb. 23, 2015

(87) PCT Pub. No.: WO2014/076818
PCT Pub. Date: May 22, 2014

(65) Prior Publication Data
US 2015/0301009 A1 Oct. 22, 2015

(51) Int. Cl.
*G01N 33/00* (2006.01)
*F01N 3/023* (2006.01)
(Continued)

(52) U.S. Cl.
CPC ......... *G01N 33/0047* (2013.01); *F01N 3/021* (2013.01); *F01N 3/023* (2013.01);
(Continued)

(58) Field of Classification Search
CPC ... F01N 3/0842; F01N 2570/14; F01N 3/0231
See application file for complete search history.

(56) References Cited

U.S. PATENT DOCUMENTS 5,651,248 A * 7/1997 Kawamura ........ B01D 46/0063
55/283
2001/0052232 A1* 12/2001 Hoffmann et al. B01D 53/9431
60/285
(Continued)

FOREIGN PATENT DOCUMENTS

CN 101743386 A 6/2010
JP 2003-176714 6/2003
(Continued)

*Primary Examiner* — Sean E Conley
*Assistant Examiner* — Matthew Krcha
(74) *Attorney, Agent, or Firm* — Finnegan, Henderson, Farabow, Garrett & Dunner, LLP

(57) ABSTRACT

In an internal combustion engine, a hydrocarbon feed valve (15), $NO_x$ storage catalyst (13), particulate filter (14), and electric resistance type sensor (29) are arranged in an engine exhaust passage in this order from an upstream side. The electric resistance type sensor (29) generates an output value corresponding to the amounts of deposition of particulate matter and hydrocarbons which are contained in the exhaust gas and deposited at the sensor part thereof. From the change of the output value of the electric resistance type sensor (29), it is judged if the hydrocarbons have slipped through the $NO_x$ storage catalyst (13) and if the particulate matter has slipped through the particulate filter (14).

11 Claims, 12 Drawing Sheets

(51) Int. Cl.
  *F01N 3/08* (2006.01)
  *F01N 11/00* (2006.01)
  *F01N 3/021* (2006.01)
  *G01N 15/06* (2006.01)
  *G01N 15/00* (2006.01)

(52) U.S. Cl.
  CPC ............ *F01N 3/0814* (2013.01); *F01N 11/00* (2013.01); *G01N 33/0036* (2013.01); *G01N 33/0037* (2013.01); *F01N 2550/00* (2013.01); *F01N 2550/02* (2013.01); *F01N 2550/04* (2013.01); *F01N 2560/023* (2013.01); *F01N 2560/05* (2013.01); *F01N 2560/12* (2013.01); *F01N 2900/0418* (2013.01); *F01N 2900/1618* (2013.01); *G01N 15/0606* (2013.01); *G01N 15/0656* (2013.01); *G01N 2015/0046* (2013.01); *Y02T 10/47* (2013.01)

(56) References Cited

U.S. PATENT DOCUMENTS

| | | | |
|---|---|---|---|
| 2002/0124551 A1* | 9/2002 | Birkhofer et al. | B01D 53/9409 60/277 |
| 2002/0194839 A1* | 12/2002 | Bidner et al. | F01N 3/0842 60/285 |
| 2008/0173009 A1* | 7/2008 | Kocher et al. | F01N 3/0814 60/286 |
| 2010/0186377 A1* | 7/2010 | Shibata et al. | F01N 3/0842 60/275 |
| 2011/0265551 A1* | 11/2011 | Hopka et al. | F01N 3/021 73/23.31 |
| 2012/0131908 A1 | 5/2012 | Bisaiji et al. | |

FOREIGN PATENT DOCUMENTS

| | | |
|---|---|---|
| JP | 2007-40130 | 2/2007 |
| JP | 2009-144577 | 7/2009 |

* cited by examiner

FIG. 1
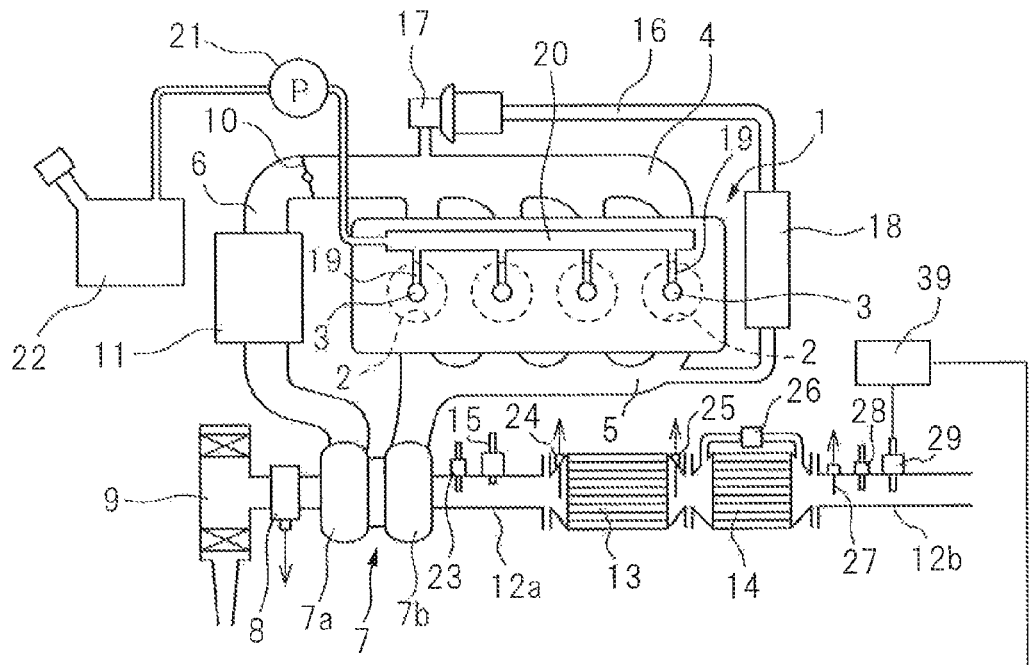
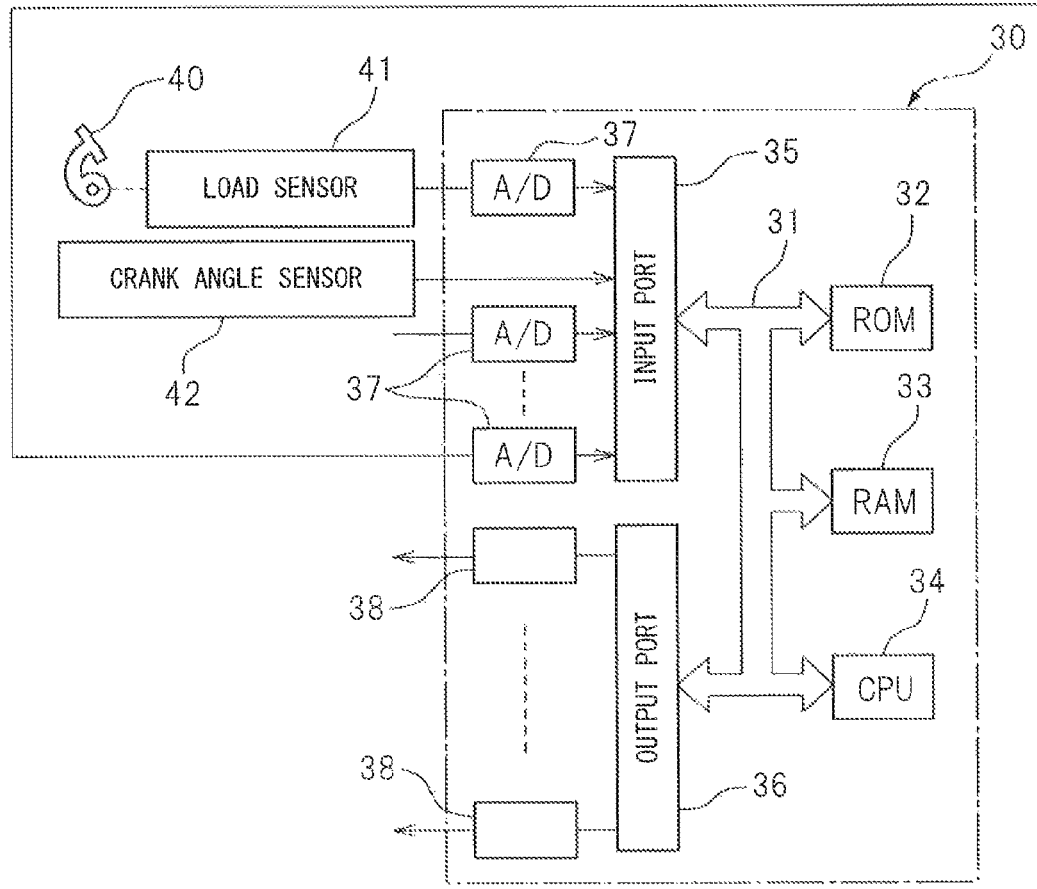

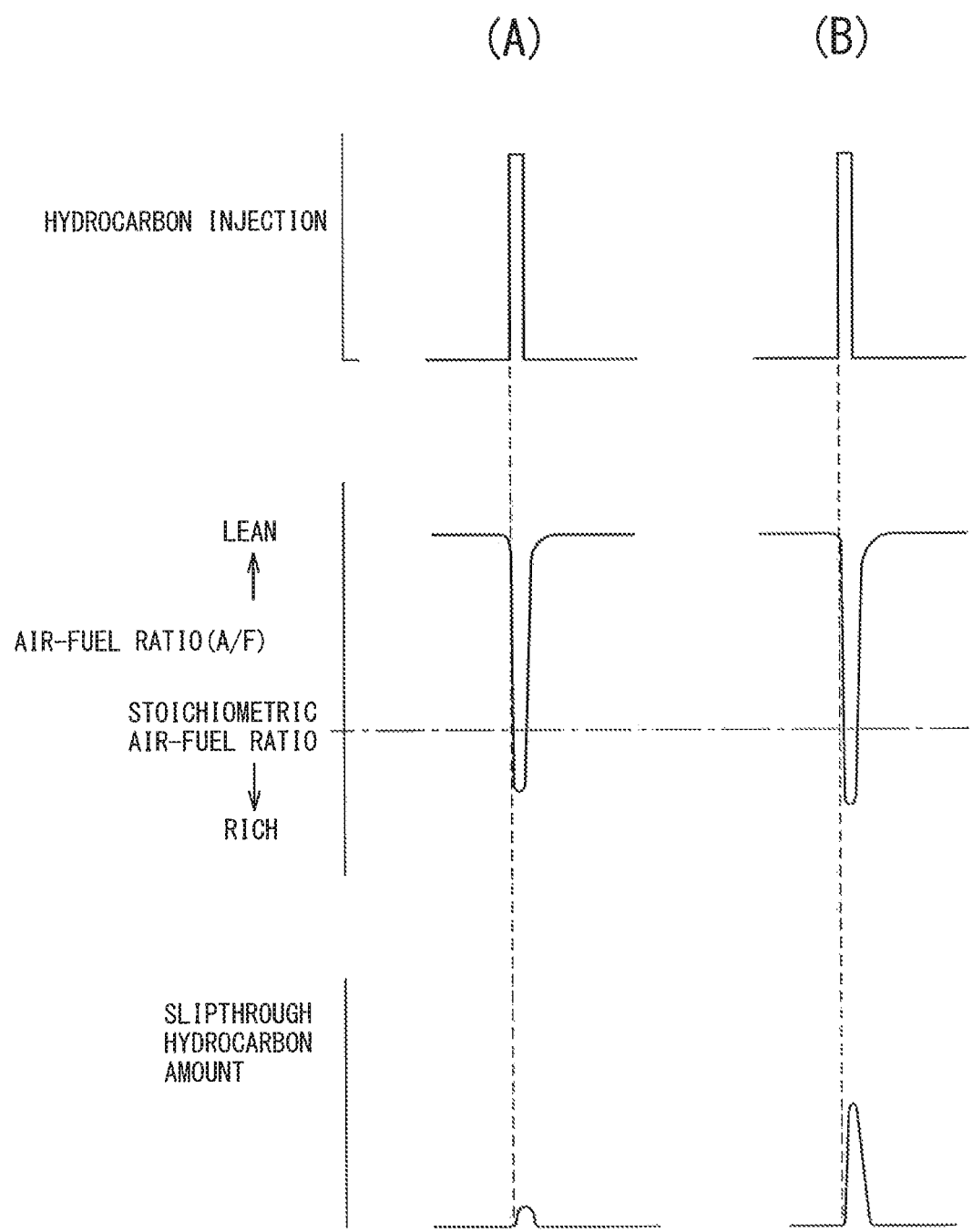

ABNORMALITY DETECTION SYSTEM OF ENGINE EXHAUST SYSTEM

CROSS-REFERENCE TO RELATED APPLICATIONS

This application is a national phase application of International Application No. PCT/JP2012/079814, filed Nov. 16, 2012, the content of which is incorporated herein by reference.

TECHNICAL FIELD

The present invention relates to an abnormality detection system of an engine exhaust system.

BACKGROUND ART

Known in the art is an internal combustion engine which arranges a particulate filter in an engine exhaust passage and which arranges a particulate matter sensor in the engine exhaust passage downstream of the particulate filter so as to detect particulate matter contained in the exhaust gas which slips through the particulate filter without being trapped by the particulate filter (for example, see PTL 1). In this internal combustion engine, this particulate matter detection sensor is used for example to detect if the particulate filter has cracked and thereby a large amount of particulate matter slips through the particulate filter, that is, the particulate filter has become abnormal.

CITATION LIST

Patent Literature

PTL 1. JP 2009-144577 A

SUMMARY OF INVENTION

Technical Problem

On the other hand, in case where an $NO_x$ storage catalyst able to store $NO_x$ when an air-fuel ratio of exhaust gas is lean and able to release stored $NO_x$ by making the air-fuel ratio of the exhaust gas rich is arranged in an engine exhaust passage, a hydrocarbon feed valve is arranged in the engine exhaust passage upstream of the $NO_x$ storage catalyst, and hydrocarbons are injected from the hydrocarbon feed valve to make the air-fuel ratio of the exhaust gas flowing into the $NO_x$ storage catalyst rich when $NO_x$ should be released from the $NO_x$ storage catalyst, if the $NO_x$ storage catalyst deteriorates, the hydrocarbons injected from the hydrocarbon feed valve will slip through the $NO_x$ storage catalyst. In this case, if it were possible to detect that hydrocarbons had slipped through the $NO_x$ storage catalyst, it would be possible to detect that the $NO_x$ storage catalyst deteriorates.

In this regard, in this case, if viewed from the viewpoint of simplification of the detection system and reduction of the manufacturing cost, it can be said to be desirable to detect the particulate matter which slips through the particulate filter and the hydrocarbons which slip through the $NO_x$ storage catalyst by a single sensor. However, the particulate matter which slips through the particulate filter and the hydrocarbons which slip through the $NO_x$ storage catalyst differ in properties. Therefore, up to now, it was never considered at all to simultaneously detect these particulate matter and hydrocarbons by a single sensor.

Therefore, the inventors engaged in repeated studies on the differences in properties between the particulate matter which slips through the particulate filter and the hydrocarbons which slip through the $NO_x$ storage catalyst and as a result discovered it is possible to detect these particulate matter and hydrocarbons by a single sensor Therefore, an object of the present invention is to provide an abnormality detection system of an engine exhaust system which is able to detect the particulate matter which slips through the particulate filter and the hydrocarbons which slip through the $NO_x$ storage catalyst by a single sensor.

Solution to Problem

According to the present invention, there is provided an abnormality detection system of an engine exhaust system in an internal combustion engine in which an $NO_x$ storage catalyst able to store $NO_x$ when an air-fuel ratio of exhaust gas is lean and able to release stored $NO_x$ by making the air-fuel ratio of the exhaust as rich is arranged in an engine exhaust passage, a hydrocarbon feed valve is arranged in the engine exhaust passage upstream of the $NO_x$ storage catalyst, a particulate filter for trapping particulate matter contained in the exhaust gas is arranged in the engine exhaust passage downstream of the $NO_x$ storage catalyst, and hydrocarbons are injected from the hydrocarbon feed valve to make the air-fuel ratio of the exhaust gas flowing into the $NO_x$ storage catalyst rich when $NO_x$ should be released from the $NO_x$ storage catalyst, wherein an electric resistance type sensor having a sensor part to which particulate matter and hydrocarbons which are contained in exhaust gas deposit and generating an output value corresponding to an amount of deposition of the particulate matter and hydrocarbons to the sensor part is arranged in the engine exhaust passage downstream of the particulate filter, the output value of the electric resistance type sensor when hydrocarbons are injected from the hydrocarbon feed valve to release $NO_x$ from the $NO_x$ storage catalyst and when hydrocarbons slip through the $NO_x$ storage catalyst exhibits a behavior which changes by a faster speed compared with when particulate matter slips through the particulate filter, then changes in direction of change to an opposite direction, and, when the output value of the electric resistance type sensor changes, it is judged if hydrocarbons have slipped through the $NO_x$ storage catalyst when hydrocarbons are injected from the hydrocarbon feed valve or particulate matter has slipped through the particulate filter from the difference in behavior of the output value of the electric resistance type sensor.

Advantageous Effects of Invention

It is possible to detect the particulate matter which slips through the particulate filter and the hydrocarbons which slip through the $NO_x$ storage catalyst by a single electric resistance type sensor and therefore it is possible to simplify the detection system and possible to reduce the manufacturing cost.

BRIEF DESCRIPTION OF DRAWINGS

FIG. 1 is an overall view of a compression ignition type internal combustion engine.

FIG. 6 is is view for explaining the amount of hydrocarbons etc. which slip through the $NO_x$ storage catalyst.

DESCRIPTION OF EMBODIMENTS

Figure 2A:
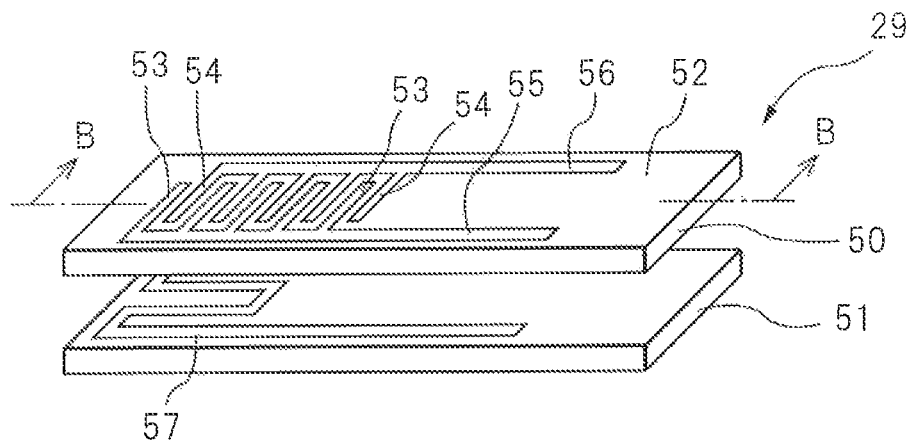
FIGS. 2A and 2B are views which show an electric resistance type sensor according to the present invention.

FIG. 1 is an overall view of a compression ignition type internal combustion engine. Referring to FIG. 1, 1 indicates an engine body, 2 a combustion chamber of each cylinder, 3 an electronically controlled fuel injector for injecting fuel into each combustion chamber 2, 4 an intake manifold, and 5 en exhaust manifold. The intake manifold 4 is connected through an intake duct 6 to the outlet of a compressor 7a of an exhaust turbocharger 7, while the inlet of the compressor 7a is connected through an intake air amount detector 8 to an air cleaner 9. Inside the intake duct 6, a throttle valve 10 which is driven by an actuator is arranged. Around the intake duct 6, a cooling device 11 is arranged for cooling the intake air which flows through the inside of the intake duct 6. In the embodiment which is shown in FIG. 1, the engine cooling water is guided to the inside of the cooling device 11 were the engine cooling water is used to cool the intake air.

On the other hand, the exhaust manifold 5 is connected to the inlet of an exhaust turbine 7b of the exhaust turbocharger 7, and the outlet of the exhaust turbine 7b is connected through an exhaust pipe 12a to the inlet of an $NO_x$ storage catalyst 13. A particulate filter 14 for trapping the particulate matter PM contained in the exhaust gas is arranged downstream of the $NO_x$ storage catalyst 13, and the outlet of the particulate filter 14 is connected to an exhaust pipe 12b. Upstream of the $NO_x$ storage catalyst 13 inside the exhaust pipe 12a, a hydrocarbon feed valve 15 is arranged for feeding hydrocarbons comprised of diesel oil or other fuel used as fuel for a compression ignition type internal combustion engine. In the embodiment shown in FIG. 1, diesel oil is used as the hydrocarbons which are fed from the hydrocarbon feed valve 15.

On the other hand, the exhaust manifold 5 and the intake manifold 4 are connected with each other through an exhaust gas recirculation (hereinafter referred to as an "EGR") passage 16. An electronically controlled EGR control valve 17 is arranged in the EGR passage 16, and around the EGR passage 16, a cooling device 18 is arranged for cooling the exhaust gas which flows through the inside of the EGR passage 16. In the embodiment which is shown in FIG. 1, the engine cooling water is guided to the inside of the cooling device 18 where the engine cooling water is used to cool the exhaust gas. Further, each fuel injector 3 is connected through a fuel feed tube 19 to a common rail 20. This common rail 20 is connected through an electronically controlled variable discharge fuel pump 21 to a fuel tank 22. The fuel which is stored inside of the fuel tank 22 is fed by the fuel pump 21 to the inside of the common rail 20. The fuel which is fed to the inside of the common rail 20 is fed through each fuel feed tube 19 to the fuel injector 3.

An electronic control unit 30 is comprised of a digital computer provided with a ROM (read only memory) 32, a RAM (random access memory) 33, a CPU (microprocessor) 34, an input port 35, and an output port 36, which are connected with each other by a bidirectional bus 31. An air-fuel ratio sensor 23 is arranged in the exhaust pipe 12a upstream of the $NO_x$ storage catalyst 13, and a temperature sensor 24 is arranged at the inlet portion of the $NO_x$ storage catalyst 13. In addition, a temperature sensor 25 is arranged also at the outlet portion of the $NO_x$ storage catalyst 13. Furthermore, a pressure difference sensor 26 for detecting the pressure difference between before and after the particulate filter 14 is attached to the particulate filter 14. On the hand, a temperature sensor 27, an air-fuel ratio sensor 28 and an electric resistance type sensor 29 for detecting the particulate matter PM and the hydrocarbon HC are arranged in the exhaust pipe 12b downstream of the particular filter 14.

The output signals of the air-fuel ratio sensors 23, 28, the temperature sensors 24, 25, 27, the pressure difference sensor 26 and the intake air amount detector 8 are input through respectively corresponding AD converters 37 to the input port 35. In addition, the output signal of a detection circuit 39 of the electric resistance type sensor 29 is also input through a corresponding AD converter 37 to the input port 35. Further, the accelerator pedal 40 has a load sensor 41 connected to it which generates an output voltage proportional to the amount of depression L of the accelerator pedal 40. The output voltage of the load sensor 41 is input, through a corresponding AD converter 37 to the input port 35. Furthermore, at the input port 35, a crank angle sensor 42 is connected which generates an output pulse every time a crankshaft rotates by, for example, 15°. On the other hand, the output port 36 is connected through corresponding drive circuits 38 to each fuel injector 3, actuator for driving the throttle valve 10, hydrocarbon feed valve 15, EGR control valve 17 and fuel pump 21.

First, referring to FIGS. 2A and 2B, the electric resistance type sensor 29 which is arranged in the exhaust pipe 12b will be explained. FIG. 2A is a disassembled perspective view of a sensor part of an electric resistance type sensor 29. As shown in FIG. 2A, the sensor part of the electric resistance type sensor 29 is, for example, comprised of a pair of plate-shaped electrical insulators 50, 51 made of alumina. The surface 52 of the electrical insulator 50 which is positioned at the opposite side to the electrical insulator 51 is exposed to the exhaust gas which flows through the inside of the exhaust pipe 12b. The electrical insulator 51 is made to closely contact the back surface of the electrical insulator 50 which is positioned at the electrical insulator 51 side. On the surface 52 of the electrical insulator 50 which is exposed to the exhaust gas, strip-shaped positive electrodes 53 and strip-shaped negative electrodes 54 are alternately arranged at equal intervals. First end parts of the positive electrodes 53 are connected to a common electrode terminal 55 which extends in the long direction of the electrical insulator 50, while first end parts of the negative electrodes 54 are connected to a common electrode terminal 56 which extends in the long direction of the electrical insulator 50. Therefore, the overall shape of the positive electrodes 53 and the overall shape of the negative electrodes 54 are both comb shapes. On the other hand, a thin film electric heater 57 is formed on the surface of the electrical insulator 51 at the electrical insulator 50 side.

Figure 2B:
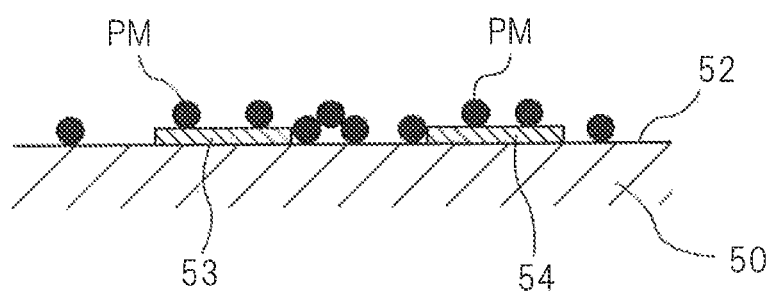

FIG. 2B is a partial cross-sectional view of the surface 52 of the electrical insulator 50 as seen along the B-B section of FIG. 2A. Note that, in FIG. 25, the black dots illustrate the particulate matter PM which deposits on the surface 52 of the electrical insulator 50. The particulate matter PM is comprised of a various of substances including carbon. This particulate matter PM has electroconductivity and has tackiness. Therefore, if exhaust gas contains particulate matter PM, the particulate matter PM gradually builds up on the surface 52 of the electrical insulator 50. If the surface 52 of the electrical insulator 50 between the strip-shaped positive electrodes 53 and the strip-shaped negative electrodes 54 is buried by the particulate matter PM, the resistance value between the positive electrodes 53 and the negative electrodes 54 will fall. That is, if the exhaust gas contains particulate matter PM, the resistance value between the positive electrodes 53 and the negative electrodes 54 will fall along with the elapse of time. Therefore, it becomes possible to detect the cumulative value of the particulate matter PM which is contained in the exhaust gas from the change in the resistance value between the positive electrodes 53 and the negative electrodes 54.

Figure 3:
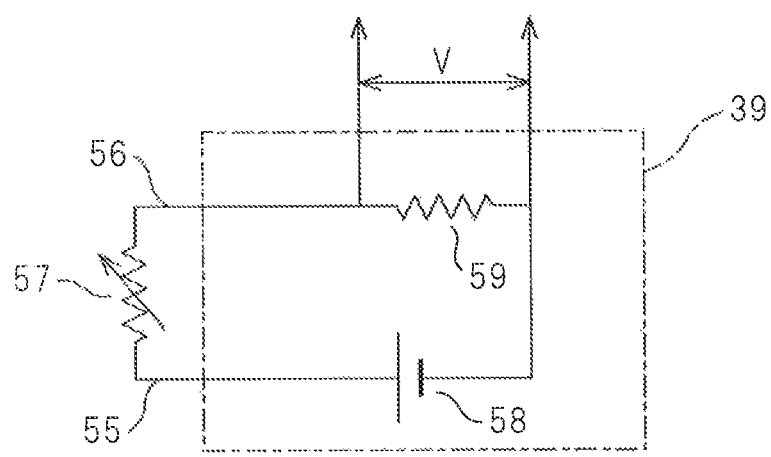
FIG. 3 is a view which shows a detection circuit of an electric resistance type sensor.

FIG. 3 shows the detection circuit 39 of the electric resistance type sensor 29. As shown in FIG. 3, the detection circuit 39 has a power source 58 and a fixed resistance 59. On the other hand, in FIG. 3, 57 shows a variable resistance which is formed by particulate matter PM between the positive electrodes 53 and negative electrodes 54. This variable resistance 57 and fixed resistance 59 are serially connected to the power source 58. If the amount of deposition of particulate matter PM to the surface 52 of the electrical insulator 50 increases, the resistance value of the variable resistance 57 becomes lower and the current which flows through the variable resistance 57 increases, so the voltage across the two ends of the fixed resistance 59 increases. The voltage across the two ends of the fixed resistance 59 is output from the detection circuit 39 as the output voltage V. Below, this output voltage V will be called the output voltage V of the electric resistance type sensor 29. Note that, the change of the resistance value of the variable resistance 57 can be taken out as the output current. Therefore, these output voltage V and output current will be referred to together as the output value of the electric resistance type sensor 29.

Figure 4A:
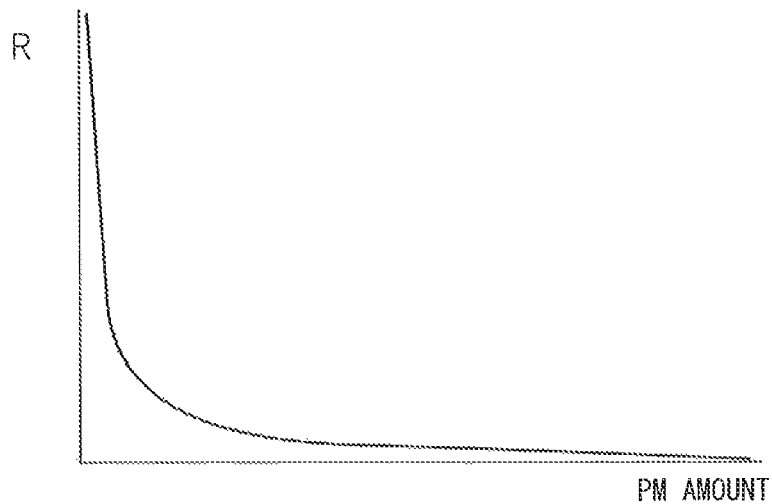
FIGS. 4A and 4B are views which show the relationship between the amount of particulate matter. PM which deposits at the sensor part of the electric resistance type sensor and the resistance value R and the relationship between the amount of particulate matter PM which deposits at the sensor part of the electric resistance type sensor and the output voltage V.
Figure 4B:
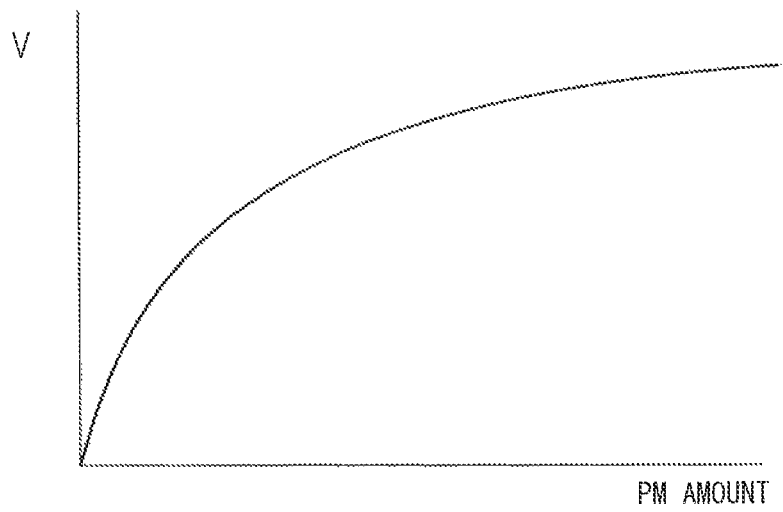

FIG. 4A shows the relationship between the amount of particulate matter PM which deposits on the sensor part of the electric resistance type sensor 29 and the resistance value R between the positive electrodes 53 and the negative electrodes 54, while FIG. 4B shows the relationship between the amount of particulate matter PM which is deposited on the sensor part of the electric resistance type sensor 29 and the output voltage V of the electric resistance type sensor 29. As will be understood from FIG. 4A, the more the amount of particulate matter PM which deposits on the sensor part of the electric resistance type sensor 29 increases, the more the resistance value R between the positive electrodes 53 and the negative electrodes 54 fall and, as will be understood from FIG. 4B, the more the amount of particulate matter PM which deposits on the sensor part of the electric resistance type sensor 29 increases, the more the output voltage V of the electric resistance type sensor 29 increases.

Figure 5A:
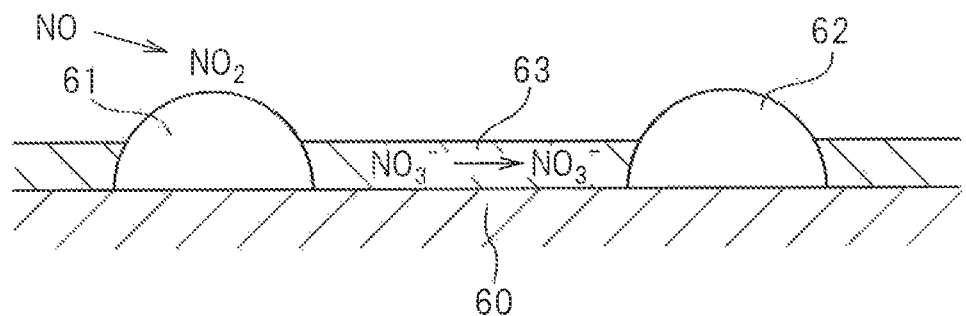
FIG. 5A and 5B are views for explaining an oxidation reduction reaction in an $NO_x$ storage catalyst.
Figure 5B:
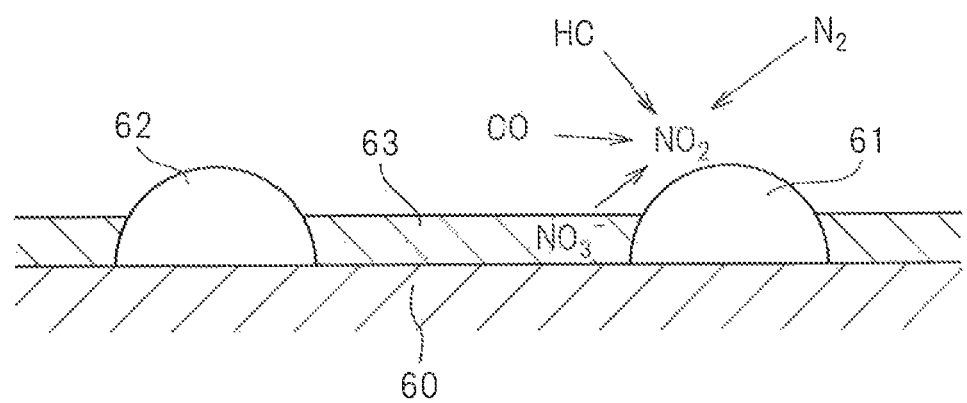

Next, a function of the $NO_x$ storage catalyst 13 will be explained. FIGS. 5A and 5B schematically shows a surface part of a catalyst carrier which is carried on a substrate of the $NO_x$ storage catalyst 13. At this $NO_x$ storage catalyst 13, as shown in FIGS. 5A and 5B, for example, there is provided a catalyst carrier 60 made of alumina on which precious metal catalysts 61 and 62 are carried. Furthermore, on this catalyst carrier 60, a basic layer 63 is formed which includes at least one element selected from potassium K, sodium Na, cesium Cs, or another such alkali metal, barium Ba, calcium Ca, or another such alkali earth metal, a lanthanide or another such rare earth and silver Ag, copper Cu, iron Fe, iridium Ir, or another metal able to donate electrons to $NO_x$.

On the other hand, in FIG. 5A and 5B, the precious metal catalyst 61 is comprised of platinum Pt, while the precious metal catalyst 62 is comprised of rhodium Rh. Note that, in this case, both the precious metal catalysts 61 and 62 may be comprised of platinum Pt. Further, on the catalyst carrier 60 of the $NO_x$ storage catalyst 13, in addition to platinum Pt and rhodium Rh, palladium Pd may be further carried or, instead of rhodium Rh, palladium Pd may be carried. That is, the precious metal catalysts 61 and 62 which are carried on the catalyst carrier 60 are comprised, of at least one of platinum Pt, rhodium Rh and palladium Pd.

Now, when the air-fuel ratio of the exhaust gas which flows into the $NO_x$ storage catalyst 13 is lean, as shown in FIG. 5A, part of the NO which is contained in the exhaust gas is oxidized on the platinum 61 and becomes $NO_2$. Next, this $NO_2$ is further oxidized and absorbed in the basic layer 63 in the form of nitrate ions $NO_3^-$. Next, the nitrate ions $NO_3^-$ diffuses in the basic layer 63 and becomes nitrates. That is, at this time, the $NO_x$ in the exhaust gas is absorbed in the form of nitrates inside of the basic layer 63. However, if the amount of the $NO_x$ absorbed in the form of nitrates inside of the basic layer 63 is increased, an $NO_x$ purification rate drops. Accordingly, when the amount of the $NO_x$ absorbed in the form of nitrates inside of the basic layer 63 is increased, it :is necessary to release the $NO_x$ absorbed inside of the basic layer 63 from the basic layer 63.

Figure 7A:
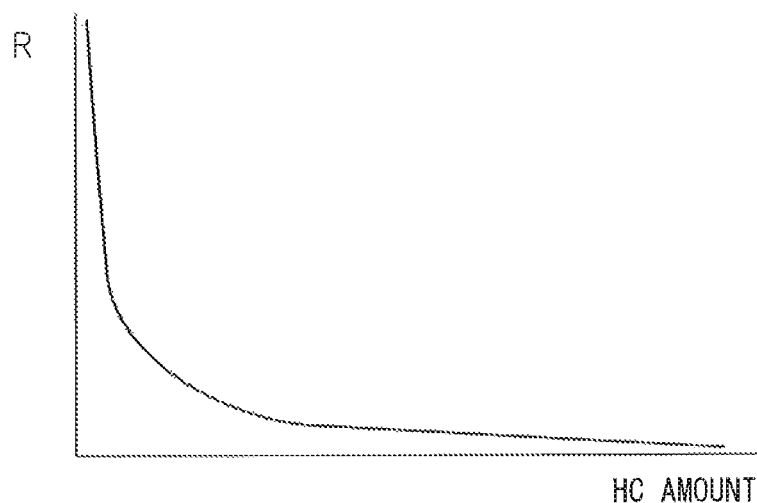
FIGS. 7A and 7B are views which show the relationship between the amount of hydrocarbons HC which deposits at the sensor part of the electric resistance type sensor and the resistance value R and the relationship between the amount of hydrocarbons HC which deposits at the sensor part of the electric resistance type sensor and the output voltage V.
Figure 7B:
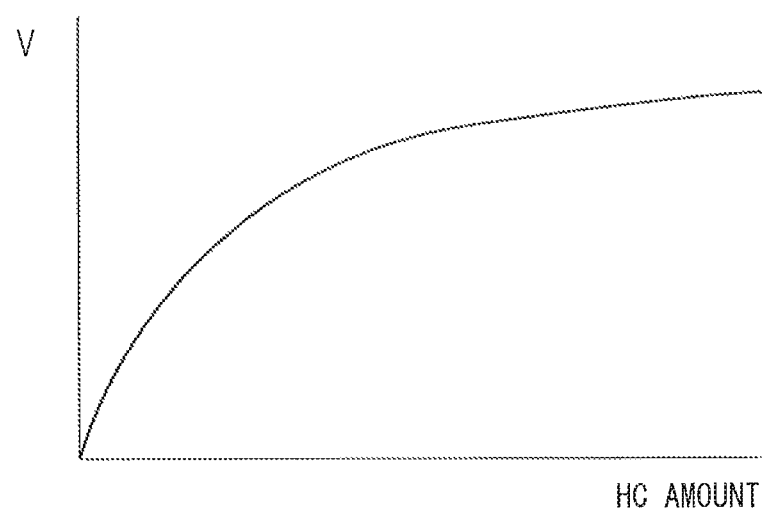

In this case, if making the air-fuel ratio of the exhaust gas which flows into the $NO_x$ storage catalyst 13 rich by feeding hydrocarbons from the hydrocarbon feed valve 15, it is possible to release the $NO_x$ absorbed inside of the basic layer 63 from the basic layer 63. FIG. 7B shows the case where the air-fuel ratio of the exhaust gas which flows into the exhaust purification catalyst 13 is made rich when the $NO_x$ is absorbed in the form of nitrates inside of the basic layer 63. In this case, the oxygen concentration in the exhaust gas falls, so the reaction proceeds in the opposite direction ($NO_3^- \rightarrow NO_2$), and consequently the nitrates absorbed in the basic layer 63 successively become nitrate ions $NO_3^-$ and, as shown in FIG. 5B, are released from the basic layer 63 in the form of $NO_2$. Next, the released $NO_2$ is reduced by the hydrocarbons HC and CO contained in the exhaust gas.

Therefore, in the present invention, the amount of $NO_x$ which is adsorbed in the form of nitrates in the basic layer 63 is estimated by for example calculation. When the amount of $NO_x$ which is adsorbed in the form of nitrates in the basic layer 63 is estimated as exceeding the allowable value, hydrocarbons are fed from the hydrocarbon feed valve 15 to make the air-fuel ratio of the exhaust gas flowing into the $NO_x$ storage catalyst 13 rich. In this case, even if making the air-fuel ratio of the exhaust gas flowing into the $NO_x$ storage catalyst 13 just slightly rich, it is not possible to make $NO_x$ be released well from the basic layer 63. To make $NO_x$ be released well from the basic layer 63, it is necessary to make the air-fuel ratio of the exhaust gas flowing into the $NO_x$ storage catalyst 13 rich to an extent required for releasing the $NO_x$ well. The injection amount of the hydrocarbons from the hydrocarbon feed valve 15 which makes the air-fuel ratio of the exhaust gas flowing into the $NO_x$ storage catalyst 13 rich to an extent required for good release of $NO_x$ is stored as a function of for example the injection amount Q from the fuel injector 3 and the engine speed N in the form of a map in advance in the ROM 32.

Now then, usually, if injecting hydrocarbons from the hydrocarbon feed valve 15 by an injection amount stored in the map, $NO_x$ can be made to be released from the basic layer 63 well. At this time, the air-fuel ratio (A/F) of the exhaust gas which flows into the $NO_x$ storage catalyst 13 and the amount of hydrocarbons which slips through the $NO_x$ storage catalyst 13 are shown in FIG. 6(A). From FIG. 6(A), it will be understood that at this time, almost no hydrocarbons slip through the $NO_x$ storage catalyst 13. On the other hand, if the $NO_x$ storage catalyst 13 deteriorates, even if injecting hydrocarbons from hydrocarbon feed valve 15 by the injection amount which is stored in the map, it is not possible to sufficiently utilize all of the injected hydrocarbons for releasing $NO_x$. Therefore, in this case, as shown in FIG. 6(B), the amount of hydrocarbons which slip through the $NO_x$ storage catalyst 13 increases. Therefore, if able to detect the amount of hydrocarbons which slips through at this time, it is possible to judge if the $NO_x$ storage catalyst 13 deteriorates.

In this regard, when hydrocarbons are fed from the hydrocarbon feed valve 15, if the hydrocarbons slip through the $NO_x$ storage catalyst 13, the hydrocarbons which slip through deposit on the surface 52 of the electrical insulator 50 of the electric resistance type sensor 29. In this regard, the surface 52 of the electrical insulator 50 is exposed to the exhaust gas, so is high in temperature. Therefore, when there is little slipthrough of the hydrocarbons, the hydrocarbons end up burning upon depositing on the surface 52 of the electrical insulator 50. As a result, in this case, hydrocarbons will not deposit on the surface 52 of the electrical insulator 50. However, if the amount of hydrocarbons which slip through the $NO_x$ storage catalyst 13 is large, the hydrocarbons temporarily build up on the surface 52 of the electrical insulator 50. In this case, since the hydrocarbons also have electroconductivity, if a large amount of hydrocarbons deposit on the surface 52 of the electrical insulator 50, the resistance value between the positive electrodes 53 and negative electrodes 54 will fall.

On the other hand, the hydrocarbons which build up on the surface 52 of the electrical insulator 50 immediately burn upon building up and are eliminated from the surface 52 of the electrical insulator 50. Therefore, when a large amount of hydrocarbons build up on the surface 52 of the electrical insulator 50, the resistance value between the positive electrodes 53 and negative electrodes 54 temporarily falls. Therefore, when feeding hydrocarbons from the hydrocarbon feed valve 15, slipthrough of the hydrocarbons through the $NO_x$ storage catalyst 13 can be detected.

PIG. 7A shows the relationship between the amount of hydrocarbons HC which temporarily deposit on the sensor part of the electric resistance type sensor 29 and the resistance value R between the positive electrodes 53 and negative electrodes 54 at this time, while FIG. 7B shows the relationship between the amount of hydrocarbons HC which temporarily deposit on the sensor part of the electric resistance type sensor 29 and the output voltage V of the electric resistance type sensor 29 at this time. As will be understood from FIG. 7A, the more the amount of temporary deposition of hydrocarbons HC at the sensor part of the electric resistance type sensor 29 increases, the more the resistance value R between the positive electrodes 53 and the negative electrodes 54 falls. As will be understood from FIG. 7B, the more the amount of temporary deposition of hydrocarbons HC at the sensor part of the electric resistance type sensor 29 increases, the more the output voltage V of the electric resistance type sensor 29 increases.

Figure 8A:
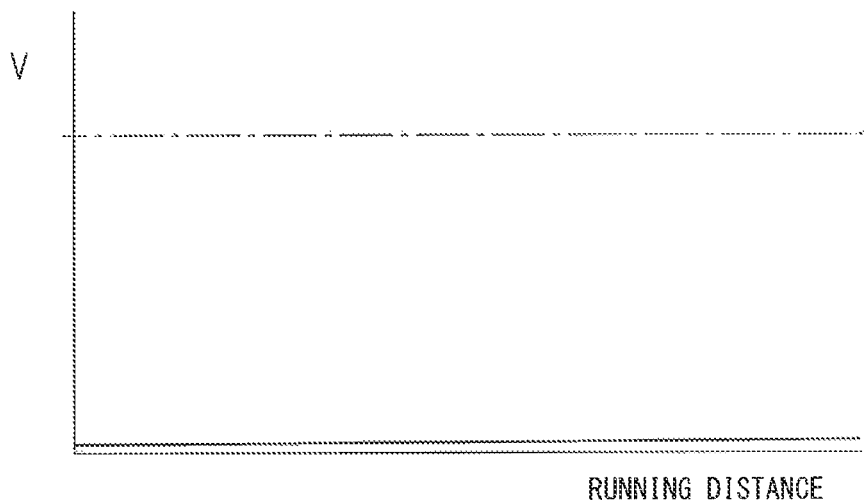
FIGS. 8A and 8B are views which show the relationship between the output voltage V of the electric resistance type sensor and the running distance of the vehicle.
Figure 8B:
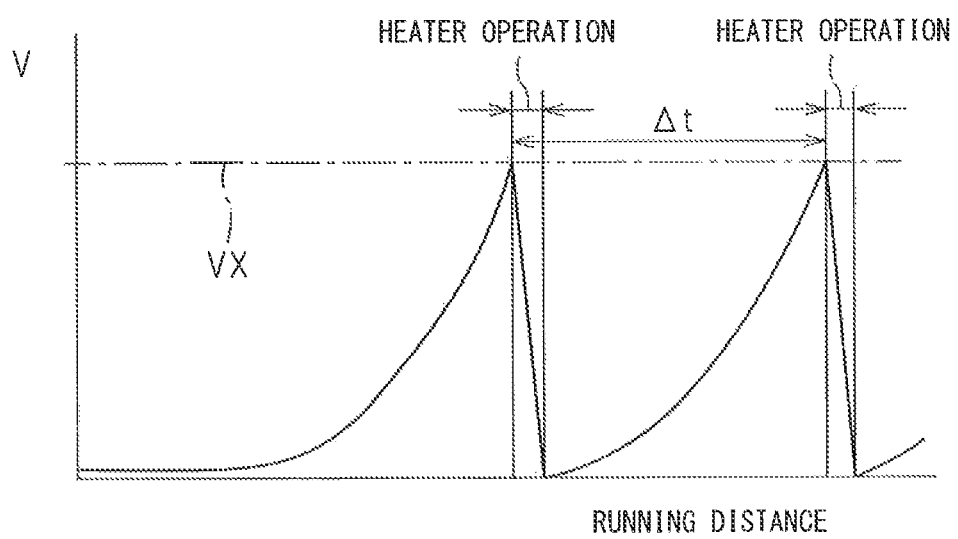

Next, referring to FIGS. 8A and 8B, slipthrough of particulate matter PM in the particulate filter 14 will be explained. Note that, FIGS. 8A and 8B show the relationship between the output voltage V of the electric resistance type sensor 29 and the running distance of the vehicle. Now then, almost all of the particulate matter PM which is contained in the exhaust gas exhausted from the engine is usually trapped by the particulate filter 14. Therefore, almost no particulate matter PM slips through the particulate filter 14. Therefore, the output voltage V of the electric resistance type sensor 29 is usually zero or, as shown in FIG. 8A, is maintained at an extremely low value.

On the other hand, when the particulate filter 14 should be regenerated, the particulate matter PM which is trapped by the particulate filter 14 is made to burn. At this time, if a situation arises at which the temperature of the particulate filter 14 becomes extremely high and after the particulate matter PM finishes being burned, the temperature of the particulate filter 14 is made to rapidly fall, the particulate filter 14 sometimes fractures, that is, cracks. If the particulate filter 14 cracks, particulate matter PM will slip through the particulate filter 14. FIG. 8B shows the case where the particulate filter 14 cracks and particulate matter PM slips through the particulate filter 14. In this case, the output voltage V of the electric resistance type sensor 29 rises to the predetermined allowable value VX in several minutes to tens of minutes in accordance with the extent of the crack.

In this embodiment according to the present invention, if the output voltage V of the detection circuit 39 rises to the allowable value VX, the electric heater 57 of the electric resistance type sensor 29 starts to be powered and the heating action of the electrical, insulator 50 is started. If the heating action of the electrical insulator 50 is started, the particulate matter PM which deposited on the surface 52 of the electrical insulator 50 is made to burn and the particulate matter PM gradually disappears from the surface 52 of the electrical insulator 50. As a result, as shown in FIG. 8B, the output voltage V of the electric resistance type sensor 29 gradually fails. Next, if the output voltage V of the electric resistance type sensor 29 becomes zero, the acting of powering the electric heater 57 is stopped. Note that, if the particulate filter 14 cracks, in the particulate filter 14, even after that, the particulate matter PM continues to slip through. As a result, the output voltage V of the electric resistance type sensor 29 again rises to the allowable value VX.

In this way, in this embodiment according to the present invention, the electric resistance type sensor 29 is provided with the electric heater 57 for heating the sensor part of the electric resistance type sensor 29. When the output value of the electric resistance type sensor 29 exceeds the predetermined allowable value VX, the heating action by the electric heater 57 is performed to burn off the particulate matter PM which deposits on this sensor part. Note that, even when the particulate filter 14 does not crack, if the vehicle is run for several thousand kilometers or more, the output voltage V of the electric resistance type sensor 29 sometimes reaches the allowable value TX. In this case as well, in the same way as the case which is shown in FIG. 8B, the electric heater 57 of the electric resistance type sensor 29 is powered and the heating action of the electrical insulator 50 is performed.

As shown in FIG. 8B, when the particulate filter 14 cracks, the output voltage V of the electric resistance type sensor 29 rises relatively slowly. Therefore, when it is judged that the output voltage V of the electric resistance type sensor 29 is gently rising as shown in FIG. 8B, it is possible to judge that the particulate filter 14 cracks, that is, the particulate filter 14 becomes abnormal. Note that, in this embodiment according to the present invention, to reliably detect that the particulate filter 14 becomes abnormal, when the period Δt (FIG. 8B) at which the heating action by the electric heater 57 is performed is shorter than a predetermined period, it is judged that the particulate filter 14 cracks, that is, that the particulate filter 14 becomes abnormal.

Figure 9:
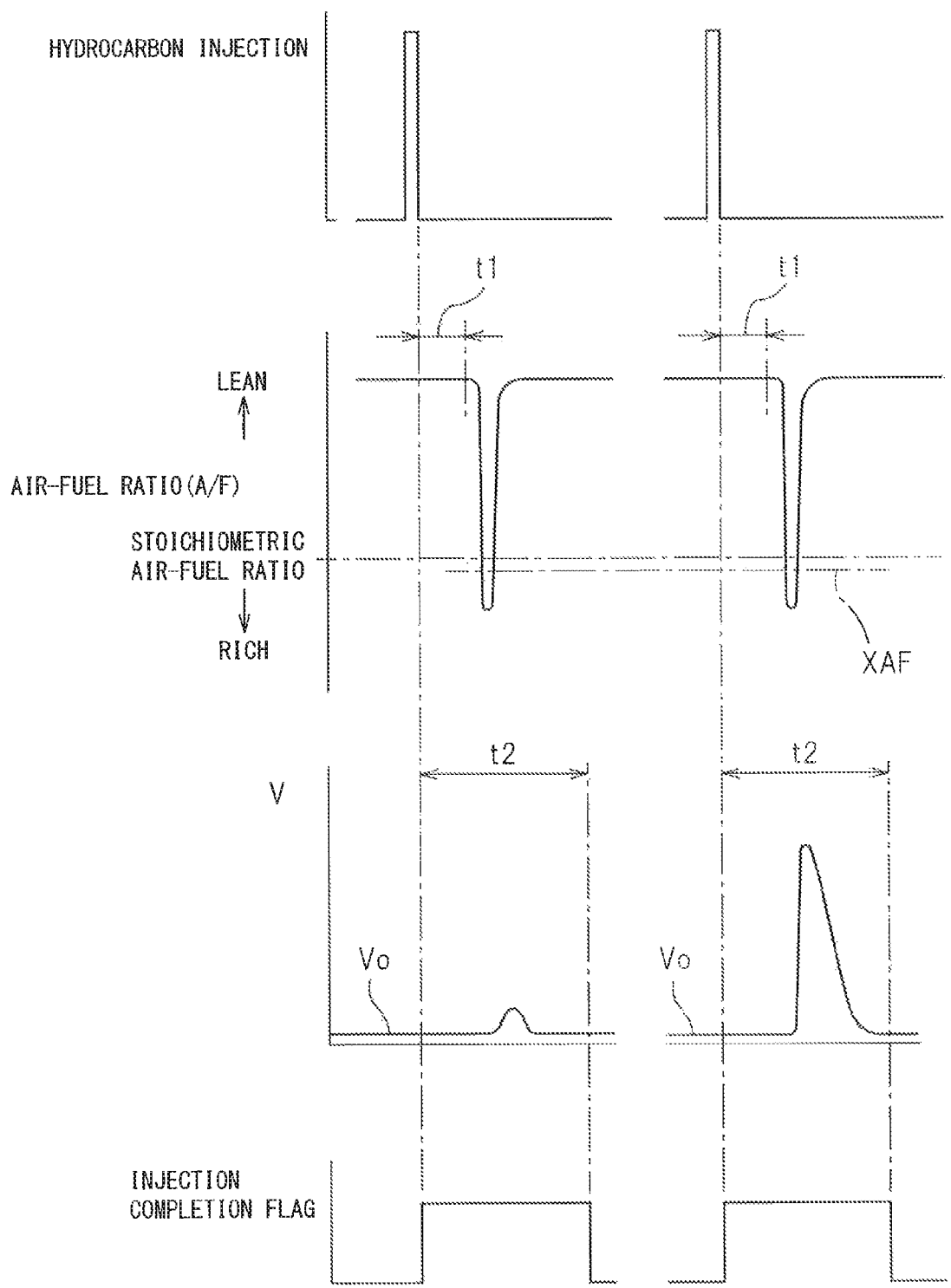
FIG. 9 is a view which shows the changes in the output voltage V of the electric resistance type sensor etc.

Next, referring to FIG. 9, the method for judging if slipthrough of the hydrocarbons is occurring at the $NO_x$ storage catalyst 13 when hydrocarbons are injected from the hydrocarbon feed valve 15 to release $NO_x$ from the $NO_x$ storage catalyst 13 will be explained. FIG. 9 shows the change in the air-fuel ratio (A/F) of the exhaust gas flowing into the $NO_x$ storage catalyst 13, the change in the output voltage V of the electric resistance type sensor 29, and the change in the injection completion flag when hydrocarbons are injected from the hydrocarbon feed valve 15 to release $NO_x$ from the $NO_x$ storage catalyst 13. Note that, FIG. 9(A) shows the case where the $NO_x$ storage catalyst 13 is not deteriorating, while FIG. 9(B) shows the case where the $NO_x$ storage catalyst 13 is deteriorating. Note that, the output voltage of the electric resistance type sensor 29 before the output voltage V of the electric resistance type sensor 29 rises due to the hydrocarbon feed valve 15 injecting hydrocarbons will be referred to below as the "reference voltage $V_0$". This reference voltage $V_0$ becomes zero when particulate matter PM is not building up on the sensor part of the electric resistance type sensor 29. On the other hand, as will he understood from FIGS. 9(A) and 9(B), the injection completion flag is set when the action of injection of hydrocarbons from the hydrocarbon feed valve 15 is completed.

As explained above, when the $NO_x$ storage catalyst 13 is not deteriorating, almost no hydrocarbons slip through the $NO_x$ storage catalyst 13 when hydrocarbons are injected from the hydrocarbon feed valve 15t to release $NO_x$ from the $NO_x$ storage catalyst 13. Therefore, in this case, as shown in FIG. 9(A), the output voltage V of the electric resistance type sensor 29 only changes a little from the reference voltage $V_0$. As opposed to this, when the $NO_x$ storage catalyst 13 deteriorates, as explained above, a large amount of hydrocarbons slips through the $NO_x$ storage catalyst 13 and, as a result, as shown in FIG. 9(B), the output voltage V of the electric resistance type sensor 29 rapidly increases from the 5reference voltage $V_0$ in from 1 second to several seconds and then decreases as the hydrocarbons which deposit on the surface 52 of the electrical insulator 50 burn.

That is, as shown in FIG. 8B, the output value of the electric resistance type sensor 29 when the particulate matter PM slips through the particulate filter 14 changes continuously toward the same direction of change. As opposed to this, as shown in FIG. 9(B), the output value of the electric resistance type sensor 29 when hydrocarbons are injected from the hydrocarbon feed valve 15 and slip through the $NO_x$ storage catalyst 13 changes by a speed faster than the speed of change of the output value of the electric resistance type sensor 29 when the particulate matter PM slips through the particulate filter 14, then changes in direction of change to the opposite direction and returns to the original output value. Further, the speed of change of the output value of the electric resistance type sensor 29 in this case is extremely fast compared with the case where the particulate filter 14 cracks.

In this way, the output value of the electric resistance type sensor 29 when hydrocarbons are injected from the hydrocarbon feed valve 15 to release $NO_x$ from the $NO_x$ storage catalyst. 13 and when the hydrocarbons HC slip through the $NO_x$ storage catalyst 13 exhibits a behavior which changes by a speed faster than when particulate matter PM slips through the particulate filter 14, then changes in direction of change to the opposite direction. Therefore, the behavior of the output value of the electric resistance type sensor 29 completely differs between when the hydrocarbons HC slip through the $NO_x$ storage catalyst 13 and the particulate matter PM slips through the particulate filter 14. Therefore, when the output value of the electric resistance type sensor 29 changes, it is possible to judge if cracking of the particulate filter 14 causes the output value of the electric resistance type sensor 29 to change or deterioration of the $NO_x$ storage catalyst 13 causes the output value of the electric resistance type sensor 29 to change from the difference of behavior of the output value of the electric resistance type sensor 29.

Therefore, in the present invention, in an internal combustion engine, an $NO_x$ storage catalyst 13 able to store $NO_x$ when an air-fuel ratio of exhaust gas is lean and able to release stored $NO_x$ by making the air-fuel ratio of the exhaust gas rich is arranged in an engine exhaust passage, a hydrocarbon feed valve 15 is arranged in the engine exhaust passage upstream of the $NO_x$ storage catalyst 13, a particulate filter 14 for trapping particulate matter PM contained in the exhaust gas is arranged in the engine exhaust passage downstream of the $NO_x$ storage catalyst 13, and hydrocarbons are injected from the hydrocarbon feed valve 15 to make the air-fuel ratio of the exhaust gas flowing into the $NO_x$ storage catalyst 13 rich when $NO_x$ should be released from the $NO_x$ storage catalyst 13, an electric resistance type sensor 29 having a sensor part to which particulate matter PM and hydrocarbons HC which are contained in exhaust gas deposit and generating an output value corresponding to an amount of deposition of the particulate matter PM and hydrocarbons HC to the sensor part is arranged in the engine exhaust passage downstream of the particulate filter 14, the output value of the electric resistance type sensor 29 when hydrocarbons are injected from the hydrocarbon feed valve 15 to release $NO_x$ from the $NO_x$ storage catalyst 13 and when hydrocarbons slip through the $NO_x$ storage catalyst 13 exhibits a behavior which changes by a faster speed compared with when particulate matter slips through the particulate filter 14, then changes in direction of change to an opposite direction, and, when the output value of the electric resistance type sensor 29 changes, it is judged if hydrocarbons have slipped through the $NO_x$ storage catalyst 13 when hydrocarbons are injected from the hydrocarbon feed valve 15 or particulate matter has slipped through the particulate filter 14 from the difference in behavior of the output value of the electric resistance type sensor 29.

In this regard, the hydrocarbon feed valve 15 and the electric resistance type sensor 29 are separated in distance, so when the hydrocarbons HC which are injected from the hydrocarbon feed valve 15 slip through the $NO_x$ storage catalyst 13, it takes time for the hydrocarbons HC to reach the electric resistance type sensor 29. In this case, the hydrocarbons which are injected from the hydrocarbon feed valve 15 reach the electric resistance type sensor 29 within a time period determined from the engine operating state after injection of hydrocarbons. In this case, to remove as much as possible the effects of outside disturbance and accurately detect the amount of hydrocarbons which slip through the $NO_x$ storage catalyst 13 by the electric resistance type sensor 29, it is preferable to find the amount of hydrocarbons which slips through from the change of the output value of the electric resistance type sensor 29 in a time period which is determined from this engine operating state.

Therefore, in the embodiment according to the present invention, when hydrocarbons are injected from the hydrocarbon feed valve 15, it is judged if hydrocarbons have slipped through the $NO_x$ storage catalyst 13 from the change in the output value of the electric resistance type sensor 29 within a time period after the injection of hydrocarbons determined from the engine operating state, that is, within a predetermined time period. Note that, the predetermined time period after injecting the hydrocarbons is the time period until the hydrocarbons injected from the hydrocarbon feed valve 15 reach and deposit on the sensor part of the electric resistance type sensor 29. Specifically speaking, the predetermined time period after injecting the hydrocarbons, as shown in FIGS. 9(A) and (B), is the time period from when the time t1 until a little before the hydrocarbons injected from the hydrocarbon feed valve 15 reach the electric resistance type sensor 29 after the injection of hydrocarbons elapses or from when the time t1 until reaching the electric resistance type sensor 29 elapses to when the time t2 from the injection of Hydrocarbons until the hydrocarbons deposited on the sensor part of the electric resistance type sensor 29 are burned away elapses. These times t1 and t2 are respectively stored as functions of for example the injection amount Q from the fuel injector 3 and the engine speed N in the form of maps in advance in the ROM 32.

Figure 10A:
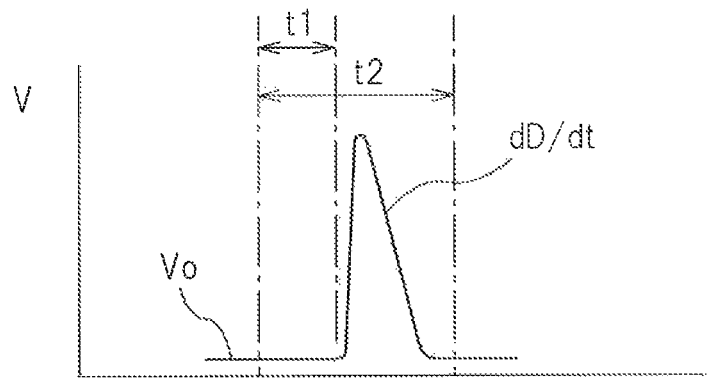
FIGS. 10A, 10B, and 10C are views which show the changes in the output voltage V of the electric resistance type sensor.

Next, referring to FIGS. 10A, 10B, and 10C which take out and show only the changes in the output voltage V which is shown in FIG. 9(B), various methods for judging slipthrough of the hydrocarbons will be explained. Now then, as explained above, the speed of change of the output value of the electric resistance type sensor 29 when hydrocarbons are injected from the hydrocarbon feed valve 15 and the hydrocarbons HC slip through the $NO_x$ storage catalyst 13 is much faster than the speed of change of the output value of the electric resistance type sensor 29 when particulate matter PM slips through the particulate filter 14. Therefore, as shown in FIG. 10A, in the first example, when the speed of change dv/dt of the output voltage V of the detection circuit 39 when rising from the reference voltage $V_0$ exceeds a set value XD, it is judged that the hydrocarbons have slipped through the $NO_x$ storage catalyst 13.

In this case, this set value XD is larger than the speed of change of the output voltage V of the electric resistance type sensor 29 when particulate matter PM slips through the particulate filter 14. Therefore, in other words, in a predetermined time period after injection of hydrocarbons (time period from elapse of t1 to elapse of t2), when the output value changes by a speed of change faster compared with the speed of change of the output value of the electric resistance type sensor 29 when particulate matter PM slips through the particulate filter 14, it is judged that the hydrocarbons have slipped through the $NO_x$ storage catalyst 13.

On the other hand, when the amount of rise of the output voltage V of the electric resistance type sensor 29 from the reference voltage V exceeds a predetermined amount $\Delta VZ$, it is possible to judge that hydrocarbons have slipped through the $NO_x$ storage catalyst 13. Therefore, in the example which is shown in FIG. 10B, when the amount of change of the output value of the electric resistance type sensor 29 exceeds the predetermined amount of change $\Delta VZ$ in a predetermined time period after injection of hydrocarbons (time period from elapse of t1 to elapse of t2), it is judged that the hydrocarbons have slipped through the $NO_x$ storage catalyst 13.

Further, the cumulative value of the amount of change of the output voltage V of the electric resistance type sensor 29 with respect to the reference voltage $V_0$ is proportional to the amount of hydrocarbons which slips through the $NO_x$ storage catalyst 13, therefore, when this cumulative amount exceeds a predetermined amount MV, it can be judged that hydrocarbons have slipped through the $NO_x$ storage catalyst 13. Therefore, in the example which is shown in FIG. 10C, in a predetermined time period after injection of hydrocarbons (time period after t1 elapses, then t2 elapses), the amount of change of the output value of the electric resistance type sensor 29 from the reference voltage $V_0$ is cumulatively added. When the cumulative value $\Sigma V$ of the amount of change of the output value exceeds the predetermined value MV, it is judged that hydrocarbons have slipped through the $NO_x$ storage catalyst.

On the other hand, when there is a request for injection of hydrocarbons from the hydrocarbon feed valve 15, if a sufficient amount of hydrocarbons is not injected due to clogging or some other such reason, even if the $NO_x$ storage catalyst 13 deteriorates, the hydrocarbons injected from the hydrocarbon feed valve 15 are only oxidized, and thus almost no hydrocarbons are exhausted from the $NO_x$ storage catalyst 13. Therefore, in this case, if using the output value of the electric resistance type sensor 29 as the basis to judge if the $NO_x$ storage catalyst 13 is deteriorating, it is mistakenly judged that the $NO_x$ storage catalyst 13 is not deteriorating. Therefore, the judgment of whether the $NO_x$ storage catalyst 13 is deteriorating has to be performed when the hydrocarbon feed valve 15 is normally injecting hydrocarbons.

In this regard, if hydrocarbons are normally injected from the hydrocarbon feed valve 15, as shown in FIGS. 9(A) and (B), the air-fuel ratio of the exhaust gas which flows out from the particulate filter 14, that is, the air-fuel ratio (A/F) which is detected by the air-fuel ratio sensor 28, becomes smaller than the predetermined air-fuel ratio XAF. Therefore, if judging whether the $NO_x$ storage catalyst 13 is deteriorating when the air-fuel ratio (A/F) which is detected by the air-fuel ratio sensor 28 becomes smaller than the predetermined air-fuel ratio XAF, there is no longer a danger of mistaken judgment. Therefore, in this embodiment according to the present invention, it is judged if hydrocarbons have slipped through the $NO_x$ storage catalyst 13 when hydrocarbons are injected from the hydrocarbon feed valve 15 and when the air-fuel ratio which is detected by the air-fuel ratio sensor 28 becomes smaller than the predetermined air-fuel ratio.

Figure 11:
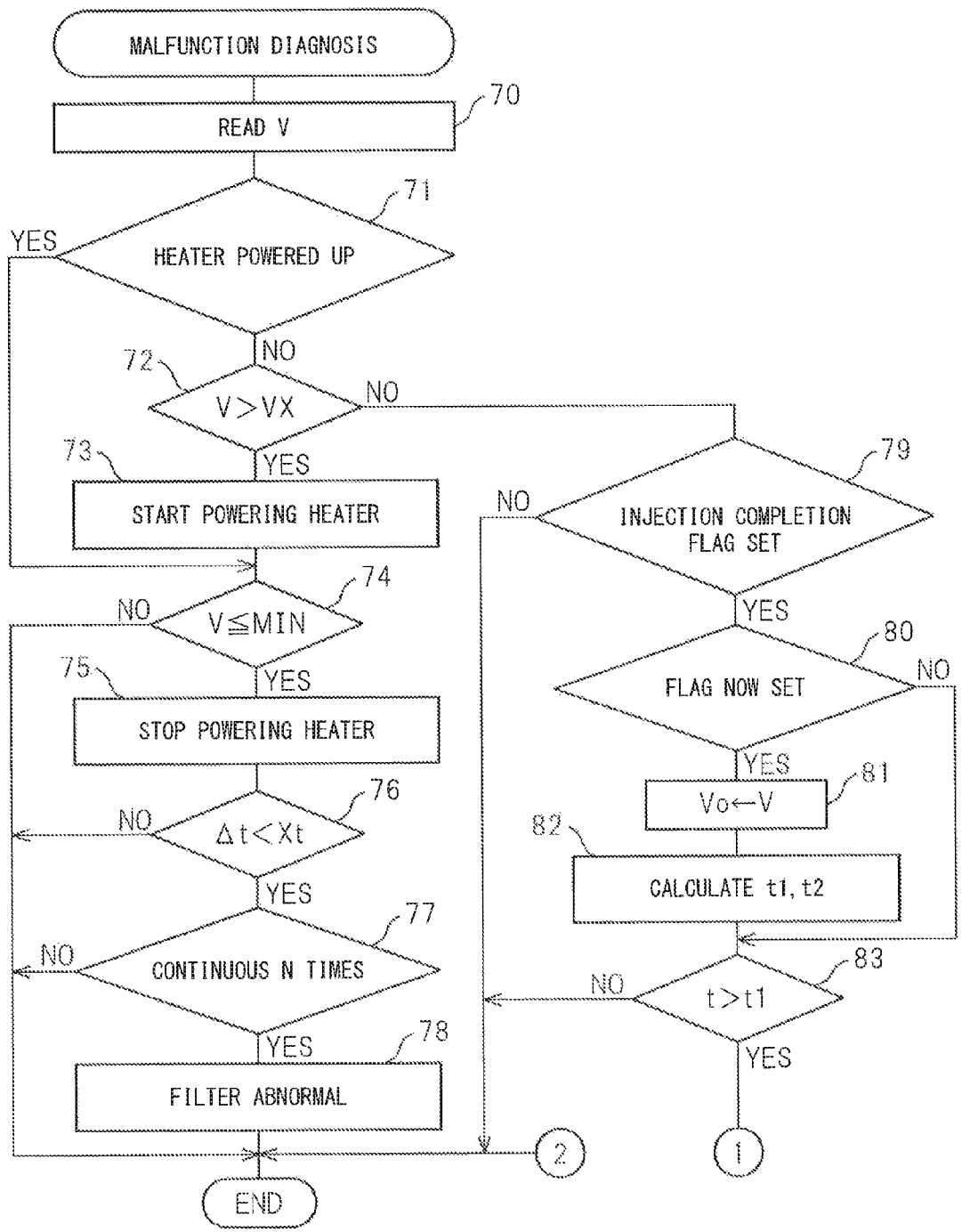
FIG. 11 is a flow chart for malfunction diagnosis.
Figure 12:
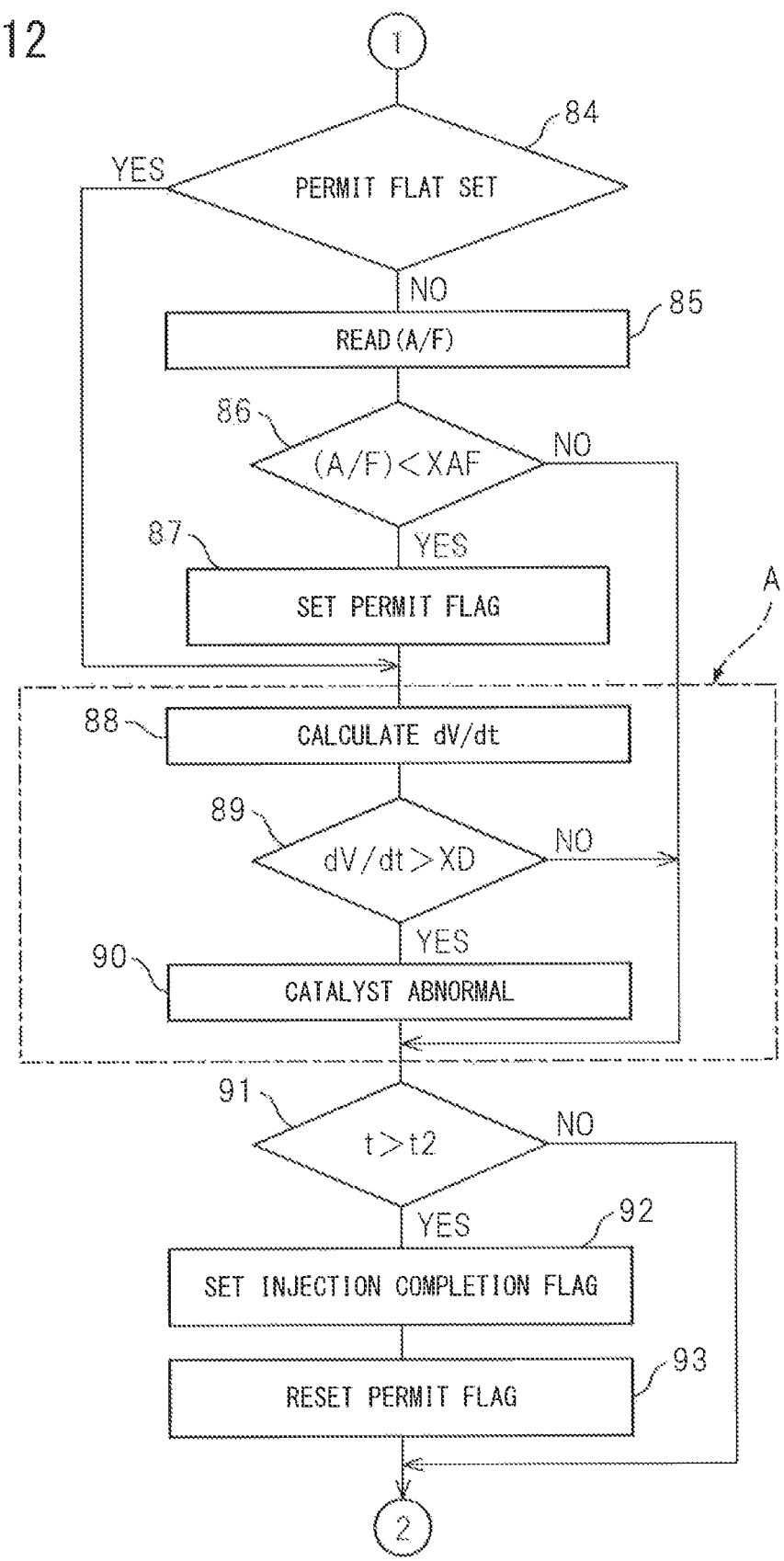
FIG. 12 is a flow chart for malfunction diagnosis.

Next, referring to FIG. 11 and FIG. 12, a routine for malfunction diagnosis for performing the example which is shown in FIG. 10A will be explained. Note that, this routine is executed by interruption every predetermined time Referring to FIG. 11, at step 70, the output voltage V of the electric resistance type sensor 29 is read. Next, at step 71, it is judged if the electric heater 57 of the electric resistance type sensor 29 is being powered. When the electric heater 57 is not being powered, the routine proceeds to step 72 where it is judged if the output voltage V of the electric resistance type sensor 29 exceeds the allowable value VX which is shown in FIG. 8B. When the output voltage V of the electric resistance type sensor 29 exceeds the allowable value VX, the routine proceeds to step 73 where the electric heater 57 of the electric resistance type sensor 29 starts to be powered. Next, the routine proceeds to step 74. If the electric heater 57 starts to be powered, at the time of the next interruption, the routine jumps from step 71 to step 74.

At step 74, it is judged if the output voltage V of the electric resistance type sensor 29 falls to zero or a minimum value MIN close to zero. When the output voltage V of the electric resistance type sensor 29 does not fall to the minimum value MIN, the processing cycle is ended, while when the output voltage V of the electric resistance type sensor 29 falls to the minimum value MIN, the routine proceeds to step 75. At step 75, the electric heater 57 is stops being powered. Next, at step 76, it is judged if the period Δt (FIG. 8B) at which the heating action by the electric heater 57 of the electric resistance type sensor 29 is performed is shorter than a predetermined period Xt. If the period Δt at which the heating action by the electric heater 57 of the electric resistance type sensor 29 is performed is shorter than the predetermined period Xt, it is provisionally judged that the particulate filter 14 is abnormal and the routine proceeds to step 77.

At step 77, it is judged if Δt<Xt stands continuously for N times or more (N being an integer of 2 or more) when the routine proceeds to step 76. When it is not judged at step 76 that Δt<Xt stands continuously for N times or more, the processing cycle is ended. As opposed to this, when it is judged at step 76 that Δt<Xt stands continuously for N times or more, the routine proceeds to step 78 where it is judged if the particulate filter 14 is abnormal. If it is judged that the particulate filter 14 is abnormal, for example, a warning lamp is turned on.

On the other hand, when, at step 72, it is judged that the output voltage V of the electric resistance type sensor 29 does not exceed the allowable value VX which is shown in FIG. 8E, the routine proceeds to step 79 where, as shown in FIG. 9, it is judged if an injection completion flag which is set when the hydrocarbon feed valve 15 finishes injecting hydrocarbons is set. When the injection completion flag is not set, the processing cycle is ended. As opposed to this, when the injection completion flag is set, the routine proceeds to step 80 where it is judged if the injection completion flag has now been set. When the injection completion flag has now been set, the routine proceeds to step 81 where the output voltage V of the electric resistance type sensor 29 is made the reference voltage $V_0$. Next, at step 82, the times t1 and t2 corresponding to the engine operating state are calculated. Next, the routine proceeds to step 83. On the other hand, when it is judged at step 80 that the injection completion flag has not been set now, the routine jumps to step 83. That is, when an injection of hydrocarbons from the hydrocarbon feed valve 15 is completed, the reference voltage $V_0$ is found and the times t1 and t2 are calculated.

At step 83, it is judged if the elapsed time from when hydrocarbons have finished being injected exceeds the time t1. When the elapsed time "t" from when hydrocarbons have finished being injected does not exceeds the time t1, the processing cycle is ended. As opposed to this, when the elapsed time "t" from when hydrocarbons finish being injected exceeds the time t1, the routine proceeds to step 84 where it is judged if a permit flag which permits judgment of whether the $NO_x$ storage catalyst 13 deteriorates is set. When the routine first proceeds to step 84 after hydrocarbons have finished being injected, the permit flag is not set, so the routine proceeds to step 85 where the air-fuel ratio (A/F) which is detected by the air-fuel ratio sensor 28 is read.

Next, at step 86, it is judged it the air-fuel ratio (A/F) detected by the air-fuel ratio sensor 28 becomes smaller than the predetermined air-fuel ratio XAF. When the air-fuel ratio (A/F) detected by the air-fuel ratio sensor 28 becomes smaller than the predetermined air-fuel ratio XAF, the routine proceeds to step 87 where the permit flag is set. Next, the routine proceeds to step 88. If the permit flag is set, in the next processing cycle, the routine jumps from step 84 to step 88. At step 88 to step 90, it is judged if the $NO_x$ storage catalyst 13 is deteriorating. Therefore, when the permit flag is set, it is learned that judgment of whether the $NO_x$ storage catalyst 13 is deteriorating is performed.

That is, at step 88, the speed of change dV/dt of the output voltage V of the electric resistance type sensor 29 is calculated. Next, at step 89, it is judged if the speed of change dV/dt of the output voltage V of the electric resistance type sensor 29 is larger than the set value XD. When the speed of change dV/dt of the output voltage V of the electric resistance type sensor 29 is larger than the set value XD, it is judged that the $NO_x$ storage catalyst 13 is deteriorating and then the routine proceeds to step 90 where it is judged that the $NO_x$ storage catalyst 13 is abnormal. If it is judged that the $NO_x$ storage catalyst 13 is abnormal, for example, a warning lamp is turned on. Next, at step 91, it is judged if the elapsed time "t" from when the hydrocarbons have finished being injected exceeds the time t2. When the elapsed time "t" from when the hydrocarbons have finished being injected exceeds the time t2, the routine proceeds to step 92 where the injection completion flag is reset. Next, the routine proceeds to step 93 where the permit flag is reset.

On the other hand, at step 89, when it is judged that the speed of change dV/dt of the output voltage V of the electric resistance type sensor 29 is smaller than the set value XD, the routine jumps to step 91. When the speed of change dV/dt of the output voltage V of the electric resistance type sensor 29 up to when the elapsed time "t" from when hydrocarbons finished being injected exceeds the time t2 does not become larger than set value XD, the routine does not proceed to step 90. Therefore, it is judged that the $NO_x$ storage catalyst 13 is not deteriorating. Note that, when it is judged at step 86 that the air-fuel ratio (A/F) which is detected by the air-fuel ratio sensor 28 does not become smaller than the predetermined air-fuel ratio XAF, the routine jumps to step 91, so at this time, judgment whether the $NO_x$ storage catalyst 13 is deteriorating is not performed.

Figure 10B:
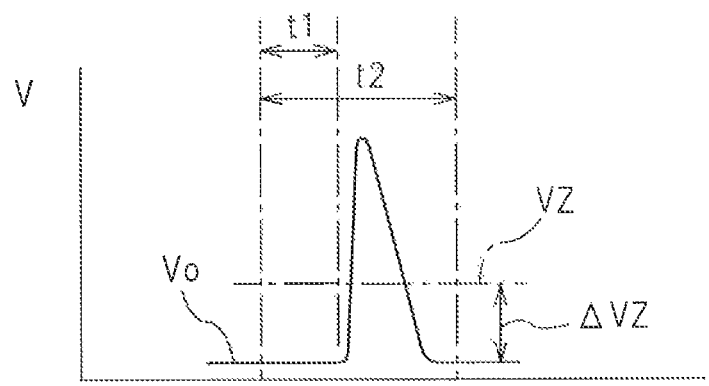
Figure 13:
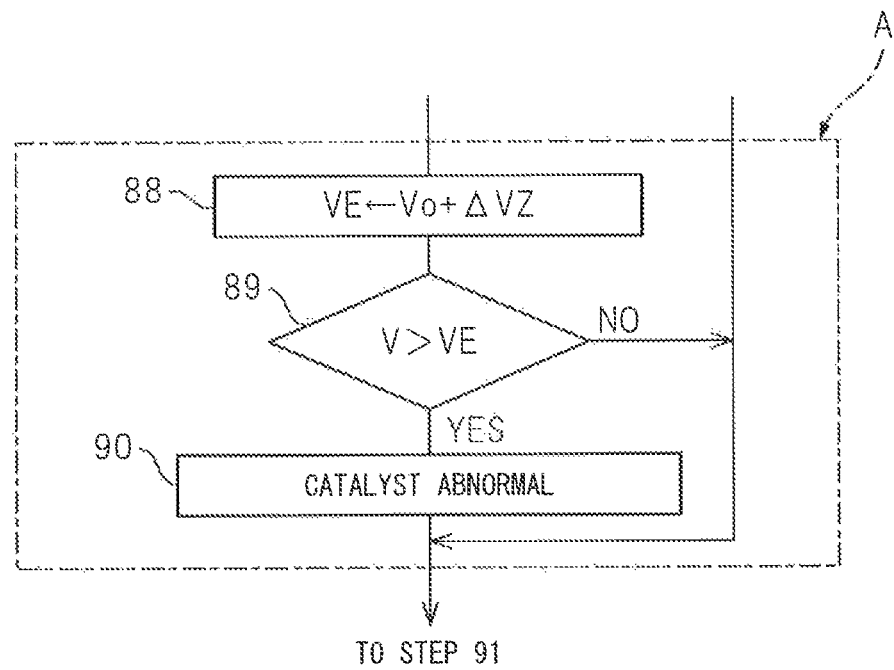
FIG. 13 is a flow chart which shows another embodiment of malfunction diagnosis which shows only a part A of the flow chart which is shown in FIG. 12.

Next, the routine for malfunction diagnosis for performing the example which is shown in FIG. 10B will be explained. In this case, as the routine for malfunction diagnosis, a routine in which steps 88 to 90 which are shown in the part surrounded by the broken line A of FIG. 12 are replaced with steps 88 to 90 of the part surrounded by the broken line A of FIG. 13 is used. Therefore, the routine for performing the example which is shown in FIG. 10B differs from the routine which is shown in FIG. 11 and FIG. 12 in only the part which is shown in FIG. 13, so below only the part which is shown in FIG. 13 will be explained.

That is, in the example which is shown in FIG. 10B, as shown in FIG. 13, first, at step 88, the predetermined amount of change ΔVZ is added to the reference voltage $V_0$ to calculate a set value VE(=$V_0$+ΔVZ). Next, at step 89, it is judged if the output voltage V of the electric resistance type sensor 29 exceeds the set value VE. When the output voltage V of the electric resistance type sensor 29 exceeds the set value VE, it is judged that the $NO_x$ storage catalyst 13 is deteriorating and the routine proceeds to step 90 where it is judged that the $NO_x$ storage catalyst 13 is abnormal. As opposed to this, when the output voltage V of the electric resistance type sensor 29 does not exceed the set value VE, the routine jumps to step 91 of FIG. 12.

Figure 10C:
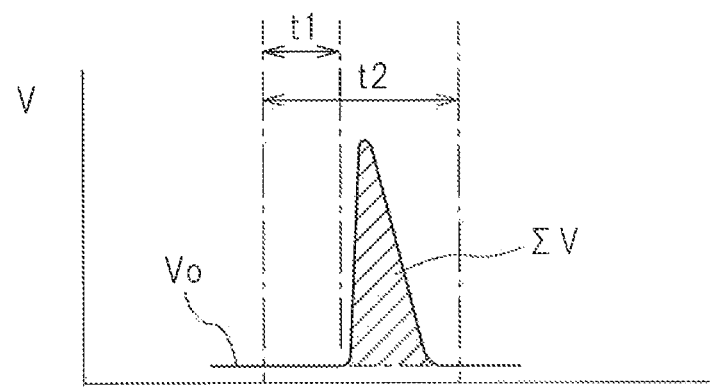

Next, the routine for malfunction diagnosis for performing the example which is shown in FIG. 10C will be explained. In this case, as the routine for malfunction diagnosis, a routine in which steps 88 to 90 which are shown in the part surrounded by the broken line A of FIG. 12 are replaced with steps 88 to 90 of the part surrounded by the broken line A of FIG. 14 is used Therefore, the routine for performing the example which is shown in FIG. 10C differs from the routine which is shown in FIG. 11 and FIG. 12 in only the part which is shown in FIG. 14, so below only the part which is shown in FIG. 14 will be explained.

Figure 14:
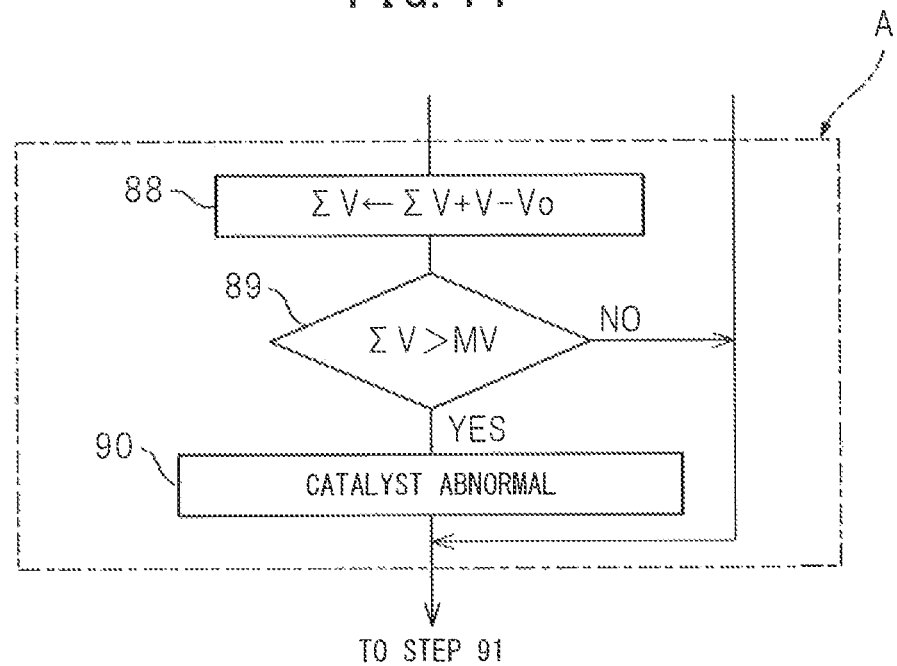
FIG. 14 is a flow chart which shows still another embodiment of malfunction diagnosis which shows only a part A of the flow chart which is shown in FIG. 12.

That is, in the example which is shown in FIG. 100, as shown in FIG. 14, first, at step 88, the value (V-$V_0$) of the output voltage V of the electric resistance type sensor 29 minus the reference voltage $V_0$ is cumulatively added and the result of cumulative addition is made the cumulative value ΣV. Next, at step 89, it is judged if the cumulative value ΣV exceeds the set value MV. When the cumulative value ΣV exceeds the set value MV, it is judged that the $NO_x$ storage catalyst 13 is deteriorating and the routine proceeds to step 90 where it is judged that the $NO_x$ storage catalyst 13 is abnormal. As opposed to this, when the cumulative value ΣV does not exceed the set value MV, the routine jumps to step 91 of FIG. 12.

EXPLANATION OF REFERENCES 4 intake manifold.
5 exhaust manifold
7 exhaust turbocharger
12a, 12b exhaust pipe
13 $NO_x$ storage catalyst
14 particulate filter
15 hydrocarbon feed valve
29 electric resistance type sensor

The invention claimed is:

1. An abnormality detection system of an engine exhaust system in an internal combustion engine in which an $NO_x$ storage catalyst able to store $NO_x$ when an air-fuel ratio of exhaust gas is lean and able to release stored $NO_x$ by making the air-fuel ratio of the exhaust gas rich is arranged in an engine exhaust passage,
    a hydrocarbon feed valve is arranged in the engine exhaust passage upstream of the $NO_x$ storage catalyst,
    a particulate filter for trapping particulate matter contained in the exhaust gas is arranged in the engine exhaust passage downstream of the $NO_x$ storage catalyst, and hydrocarbons are injected from the hydrocarbon feed valve to make the air-fuel ratio of the exhaust gas flowing into the $NO_x$ storage catalyst rich when $NO_x$ should be released from the $NO_x$ storage catalyst, the abnormality detection system comprising:
    an electronic control unit; and
    an electric resistance sensor arranged in the engine exhaust passage downstream of the particulate filter, wherein
    the electric resistance sensor includes a sensor part on which particulate matter and hydrocarbons which are contained in exhaust gas deposit, the electric resistance sensor is configured to generate an output value corresponding to an amount of deposition of the particulate matter and hydrocarbons on said sensor part,
    the electronic control unit is programmed to determine an amount of deposition of the particulate matter and hydrocarbons based on the output value of the electric resistance sensor, and
    the electronic control unit being programmed such that when the output value of the electric resistance sensor changes, the electronic control unit determines if hydrocarbons have slipped through the $NO_x$ storage catalyst when hydrocarbons are injected from the hydrocarbon feed valve or particulate matter has slipped through the particulate filter from a difference in behavior of the output value of the electric resistance sensor, wherein the difference in behavior of the output value of the electric resistance sensor when hydrocarbons are injected from the hydrocarbon feed valve to release $NO_x$ from the $NO_x$ storage catalyst and when hydrocarbons slip through the $NO_x$ storage catalyst, is the difference in behavior which changes by a faster seed compared with when particulate matter slips through the particulate filter, then changes in direction of change to an opposite direction.

2. The abnormality detection system of an engine exhaust system as claimed in claim 1, wherein the electric resistance sensor is configured such that the output value of said electric resistance sensor when the particulate matter slips through the particulate filter changes continuously toward the same direction of change, while the output value of said electric resistance sensor when hydrocarbons are injected from the hydrocarbon feed valve and slip through the $NO_x$ storage catalyst changes by a faster speed compared with the speed of change of the output value of when the particulate matter slips through the particulate filter, then changes in direction of change to the opposite direction and returns to an original output value.

3. The abnormality detection system of an engine exhaust system as claimed in claim 1, wherein when hydrocarbons are injected from the hydrocarbon feed valve, the electronic control unit is programmed to determine if hydrocarbons have slipped through the $NO_x$ storage catalyst based on the change of the output value of said electric resistance sensor in a predetermined time period after the injection of hydrocarbons.

4. The abnormality detection system of an engine exhaust system as claimed in claim 3, wherein said predetermined time period after the injection of hydrocarbons is a time period in which hydrocarbons injected from the hydrocarbon feed valve reach and deposit on the sensor part of the electric resistance sensor.

5. The abnormality detection system of an engine exhaust system as claimed in claim 3, wherein the electronic control unit is programmed to determine that hydrocarbons have slipped through the $NO_x$ storage catalyst when the output value of said electric resistance sensor changes by a speed faster than the speed of change of said output value of when the particulate matter slips through the particulate filter in said predetermined time period after the injection of hydrocarbons.

6. The abnormality detection system of an engine exhaust system as claimed in claim 3, wherein the electronic control unit is programmed to determine that hydrocarbons have slipped through the $NO_x$ storage catalyst when an amount of change of the output value of said electric resistance sensor exceeds a predetermined amount of change in said predetermined time period after the injection of hydrocarbons.

7. The abnormality detection system of an engine exhaust system as claimed in claim 3, wherein
   an amount of change of the output value of said electric resistance sensor is cumulatively added in said predetermined time period after the injection of hydrocarbons, and
   the electronic control unit is programmed to determine that hydrocarbons have slipped through the $NO_x$ storage catalyst when a cumulative value of the amount of change of the output value exceeds a predetermined value.

8. The abnormality detection system of an engine exhaust system as claimed in claim 3, wherein
   an air-fuel ratio sensor is arranged in the engine exhaust passage downstream of the $NO_x$ storage catalyst, and
   the electronic control unit is programmed to determine if hydrocarbons have slipped through the $NO_x$ storage catalyst when hydrocarbons are injected from the hydrocarbon feed valve and an air-fuel ratio detected by said air-fuel ratio sensor becomes smaller than a predetermined air-fuel ratio.

9. The abnormality detection system of an engine exhaust system as claimed in claim 1, wherein
   said electric resistance sensor has strip-shaped positive electrodes and strip-shaped negative electrodes which are alternately arranged at intervals on a surface of an electrical insulator exposed to the exhaust gas, and
   the electric resistance sensor is configured such that when particulate matter or hydrocarbons deposit on the surface of said electrical insulator, a resistance value between the positive electrodes and negative electrodes decreases.

10. The abnormality detection system of an engine exhaust system as claimed in claim 9, wherein
    said electric resistance sensor is provided with an electric heater for heating the sensor part, and
    the electric heater is configured to perform a heating action to burn off the particulate matter deposited on the sensor part when the output value of said electric resistance sensor exceeds a predetermined allowable value.

11. The abnormality detection system of an engine exhaust system as claimed in claim 10, wherein the electronic control unit is programmed to determine that the particulate filter is abnormal when a period by which the heating action by said electric heater is performed is shorter than a predetermined period.

\* \* \* \* \*